United States Patent
Hirao et al.

(10) Patent No.: US 10,398,028 B2
(45) Date of Patent: *Aug. 27, 2019

(54) SURFACE TREATING COMPOSITION FOR COPPER AND COPPER ALLOY AND UTILIZATION THEREOF

(71) Applicant: SHIKOKU CHEMICALS CORPORATION, Kagawa (JP)

(72) Inventors: Hirohiko Hirao, Kagawa (JP); Noriaki Yamaji, Kagawa (JP); Masato Nakanishi, Kagawa (JP); Takayuki Murai, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 364 days.

This patent is subject to a terminal disclaimer.

(21) Appl. No.: 15/351,898

(22) Filed: Nov. 15, 2016

(65) Prior Publication Data

US 2017/0064823 A1    Mar. 2, 2017

Related U.S. Application Data

(62) Division of application No. 14/119,304, filed as application No. PCT/JP2012/063826 on May 23, 2012, now Pat. No. 9,532,493.

(30) Foreign Application Priority Data

May 23, 2011  (JP) ................ 2011-114289

(51) Int. Cl.

| | |
|---|---|
| *H05K 3/28* | (2006.01) |
| *C23C 22/52* | (2006.01) |
| *H05K 1/09* | (2006.01) |
| *B23K 35/365* | (2006.01) |
| *C07D 233/56* | (2006.01) |
| *C07D 235/08* | (2006.01) |
| *C07D 409/04* | (2006.01) |
| *C07D 409/06* | (2006.01) |
| *C23F 11/14* | (2006.01) |
| *C23F 11/16* | (2006.01) |
| *H05K 13/00* | (2006.01) |
| *H05K 1/03* | (2006.01) |
| *C23C 22/00* | (2006.01) |
| *H05K 3/00* | (2006.01) |
| *H05K 1/00* | (2006.01) |
| *B23K 101/42* | (2006.01) |
| *B23K 103/12* | (2006.01) |

(52) U.S. Cl.
CPC ............ *H05K 1/09* (2013.01); *B23K 35/365* (2013.01); *C07D 233/56* (2013.01); *C07D 235/08* (2013.01); *C07D 409/04* (2013.01); *C07D 409/06* (2013.01); *C23C 22/52* (2013.01); *C23F 11/149* (2013.01); *C23F 11/165* (2013.01); *H05K 1/0346* (2013.01); *H05K 3/282* (2013.01); *H05K 13/00* (2013.01); *B23K 2101/42* (2018.08); *B23K 2103/12* (2018.08)

(58) Field of Classification Search
CPC ........ C23C 22/48; C23C 22/53; C23C 22/632
See application file for complete search history.

(56) References Cited

U.S. PATENT DOCUMENTS

| | | |
|---|---|---|
| 5,498,301 A | 3/1996 | Hirao et al. |
| 6,121,260 A | 9/2000 | Thurkauf et al. |
| 2003/0149089 A1 | 8/2003 | Heerding et al. |

FOREIGN PATENT DOCUMENTS

| | | |
|---|---|---|
| CN | 101448978 | 6/2009 |
| EP | 0178864 | 4/1986 |
| EP | 0364132 | 4/1990 |
| EP | 0627499 | 12/1994 |
| JP | 46-017046 | 5/1971 |
| JP | 04-206681 | 7/1992 |
| JP | 05-025407 | 2/1993 |
| JP | 05-186888 | 7/1993 |
| JP | 07-243054 | 9/1995 |
| JP | 09-291372 | 11/1997 |
| WO | 99/01128 | 1/1999 |
| WO | 2010/016620 | 2/2010 |

OTHER PUBLICATIONS

Office Action dated Sep. 17, 2018 in Vietnamese Application No. 1-2013-03704, with English translation.
Office Action dated Aug. 1, 2017 in Korean Application No. 10-2013-7031091, with English Translation.
Chinese Office Action, dated Dec. 16, 2015, in corresponding Chinese Patent Application No. 201280025100.9, with English translation.
International Search Report for PCT/JP2012/063826, dated Aug. 28, 2012.
Chinese Office Action, dated Feb. 13, 2015, in corresponding Chinese Patent Application No. 201280025100.9, with English translation.
Office Action dated Jan. 31, 2019 in corresponding Indian Patent Application No, 9996/DELNP/2013 with English translation.

*Primary Examiner* — Lois L Zheng
(74) *Attorney, Agent, or Firm* — Wenderoth, Lind & Ponack, L.L.P.

(57) ABSTRACT

A surface treating composition for copper or a copper alloy comprising an imidazole compound and means for using the composition in the soldering of electronic parts to printed wiring boards are disclosed.

6 Claims, No Drawings

SURFACE TREATING COMPOSITION FOR COPPER AND COPPER ALLOY AND UTILIZATION THEREOF

TECHNICAL FIELD

The present invention relates to a surface treating composition used in soldering electronic parts and the like to a circuit part comprising copper or a copper alloy of a printed wiring board, and utilization of the composition.

BACKGROUND ART

Recently, surface mounting with increased mounting density has been widely employed as a mounting method in the production of printed wiring boards. Such methods of surface mounting can be classified into (i) a double-sided surface mounting method of joining chip parts with a solder paste, (ii) a mixed mounting method combining surface mounting of chip parts with a solder paste and through-hole mounting of discrete parts, and the like. In each of these mounting methods, a printed wiring board is subjected to multiple rounds of soldering, and therefore, develops a severe thermal history due to repeated exposure to high temperatures.

Exposure to high temperatures can have a negative effect on the copper or copper alloy that constitutes the circuit parts of the printed wiring board due to formation of an oxide coating film on a surface of the copper or copper alloy. Repeated exposure to the high temperatures can accelerated formation of the oxide coating film. Good solderability of the surface of the circuit part cannot be maintained as the coating develops.

In order to protect the copper or copper alloy of a circuit part of such a printed wiring board from air oxidation, a treatment that produces a chemical conversion coating on the surface of the circuit part, using a surface treating composition, is widely used. It is required that the chemical conversion coating be maintained on the circuit part without modification (deterioration) even after the circuit part has received multiple thermal histories, thereby maintaining good solderability.

Eutectic solders comprising a tin-lead alloy have been widely used for joining electronic parts to a printed wiring board and the like. In recent years, however, harmful effects on the human body by lead (Pb) contained in the solder alloy have been recognized, and use of solders free of lead is now required. For this reason, various lead-free solders have been investigated. For example, lead-free solders comprising tin (Sn) as a base metal, having added thereto a metal such as silver (Ag), zinc (Zn), bismuth (Bi), indium (In), antimony (Sb), cobalt (Co), manganese (Mn), nickel (Ni), or copper (Cu), have been proposed.

The conventional Sn—Pb eutectic solder has excellent wettability to a surface of a metal, particularly copper, used in a joining base material, and strongly joins to copper. Therefore, high reliability is achieved in bondability between copper members.

In contrast, lead-free solders typically have poor wettability to a surface of copper, as compared with the conventional Sn—Pb eutectic solder, and therefore have poor solderability. As a result, joining defects, such as the occurrence of voids, are common when lead-free solders are used, which can result in low joint strength.

For this reason, selection of a solder alloy having better solderability and a flux suitable for lead-free soldering is required when lead-free solders are employed. Also, a surface treating composition that can prevent oxidation of a copper or copper alloy surface and that has the properties of improving the wettability of lead-free solder and of allowing good solderability are required.

Many lead-free solders have a high melting point, and therefore the soldering temperature is about 20° C. to 50° C. higher than that of a conventional tin-lead eutectic solder. Therefore, an improved surface treating composition would also be required to form a chemical conversion coating having excellent heat resistance.

Various imidazole compounds are proposed as an effective component of such an improved surface treating composition. For example, Patent Document 1 discloses 2-alkylimidazol compounds such as 2-undecylimidazole, Patent Document 2 discloses 2-arylimidazole compounds such as 2-phenylimidazole and 2-phenyl-4-methylimidazole, Patent Document 3 discloses 2-alkylbenzimidazole compounds such as 2-nonylbenzimidazole, Patent Document 4 discloses 2-aralkylbenzimidazole compounds such as 2-(4-chlorophenylmethyl)benzimidazole, and Patent Document 5 discloses 2-aralkylimidazole compounds such as 2-(4-chlorophenylmethyl)imidazole and 2-(2,4-dichlorophenylmethyl)-4,5-diphenylimidazole. However, when surface treating compositions containing these imidazole compounds were tested, the heat resistance of chemical conversion coatings formed on a copper surface was found to be unsatisfactory. Furthermore, when soldering was performed, the wettability of the solder was found to be insufficient, and good solderability was not obtained. Particularly, when soldering was performed on a copper surface treated with a surface treating composition comprising one of the referenced imidazole compounds and lead-free solder was used in place of tin-lead eutectic solder, acceptable results were not obtained.

CITATION LIST

Patent Document

Patent Document 1: JP-B 46-17046 (1971)
Patent Document 2: JP-A 4-206681 (1992)
Patent Document 3: JP-A 5-25407 (1993)
Patent Document 4: JP-A 5-186888 (1993)
Patent Document 5: JP-A 7-243054 (1995)

SUMMARY OF INVENTION

The present invention has been made in view of the above circumstances, with the objective of providing a surface treating composition which, upon chemical conversion when reacting with a surface of copper or a copper alloy (hereinafter sometimes merely referred to as "copper"), can form a coating having excellent properties of heat resistance and wettability to solder on the surface. The copper or copper alloy may constitute, for example, a circuit part and the like of a printed wiring board. Surface treatment using the composition of the present invention will enhance solderability when electronic parts and the like are joined to the printed wiring board using solder. The present invention also has the objective of providing a method for treating a surface of a printed wiring board, and an improved method of soldering.

As a result of keen investigations to meet the above objectives, the present inventors have developed a surface treating composition containing an imidazole compound represented by chemical formula (I). It has been found that by treating a printed wiring board having a circuit part, in particular where the circuit part constitutes copper or a copper alloy, with the surface treating composition, a chemical conversion coating having excellent heat resistance that is durable to the soldering temperature of a lead-free solder, is formed on a surface of the circuit part. Further, it has been found that by forming the chemical conversion coating, wettability of solder to the surface of the copper or the copper alloy, specifically wettability of solder to a surface of the chemical conversion coating formed on the surface of the copper or the copper alloy, is improved and good solderability to the copper or copper alloy is achieved, especially when the soldering uses a lead-free solder. In light of these findings, the present invention has been achieved.

That is, in a first aspect the present invention is directed to a surface treating composition for copper or a copper alloy, comprising an imidazole compound represented by the chemical formula (I).

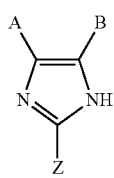
(I)

In the chemical formula (I), A represents a group represented by the following formula (II) or a group represented by formula (III), B represents a hydrogen atom, a methyl group or a phenyl group, and Z represents a group represented by formula (IV) or a group represented by formula (V),

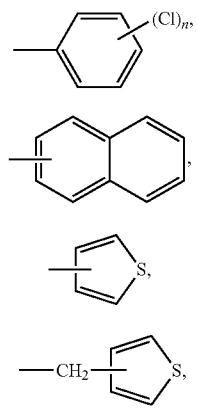

wherein n is 0, 1 or 2.

In a second aspect, the present invention is directed to a method for treating a surface of copper or a copper alloy, comprising contacting a surface of copper or a copper alloy with the surface treating composition of the first aspect of the present invention.

In a third aspect, the present invention is directed to a printed wiring board comprising at least one circuit part, wherein the circuit part comprises copper or a copper alloy and a chemical conversion coating on a surface of the copper or the copper alloy, wherein the coating is formed by contacting the surface of the copper or the copper alloy with the surface treating composition of the first aspect of the present invention.

In a fourth aspect, the present invention is directed to a method for forming a chemical conversion coating on at least one circuit part of a printed wiring board, comprising contacting at least one circuit part of a printed wiring board with the surface treating composition of the first aspect of the present invention, wherein the circuit part comprises copper or a copper alloy, thereby forming a chemical conversion coating on at least one circuit part of a printed wiring board.

In a fifth aspect, the present invention is directed to a method for soldering, comprising contacting a surface of copper or a copper alloy with the surface treating composition of the first aspect of the present invention and soldering to the copper or copper alloy.

In a sixth aspect, the present invention is directed to a method for soldering an electronic part to a circuit part of a printed wiring board, comprising (a) contacting a circuit part of a printed wiring board with the surface treating composition of the first aspect of the present invention, wherein the circuit part comprises copper or a copper alloy, and (b) soldering an electronic part to the circuit part of (a), thereby soldering an electronic part to a circuit part of a printed wiring board.

The surface treating composition of the present invention forms a chemical conversion coating having excellent heat resistance properties on a surface of copper or a copper alloy, such as a circuit part and the like of a printed wiring board that is comprised of copper or a copper alloy. Further, the coating remarkably improves the wettability of lead-free solder to the coated surface, thereby enhancing solderability to the copper or copper alloy.

Furthermore, the soldering method of the present invention enables to use of a solder which does not contain lead, which is a harmful metal, and is therefore useful from the standpoint of environmental protection.

DESCRIPTION OF EMBODIMENTS

The present invention is described in detail below.

The imidazole compounds used in the surface treating composition of the present invention are represented by the above-described chemical formula (I). The imidazole compounds have a structure wherein a thienyl group or a thienylmethyl group is bonded to the 2-position of an imidazole ring, wherein a phenyl group, a chlorophenyl group, a dichlorophenyl group, or a naphthyl group is bonded to 4 (5)-position thereof, and wherein a hydrogen atom, a methyl group or a phenyl group is bonded to 5 (4)-position thereof.

The imidazole compounds can be synthesized by, for example, employing a synthesis method shown in the following reaction scheme. As an amidine compound, an amidine hydrochloride compound can be preferably used.

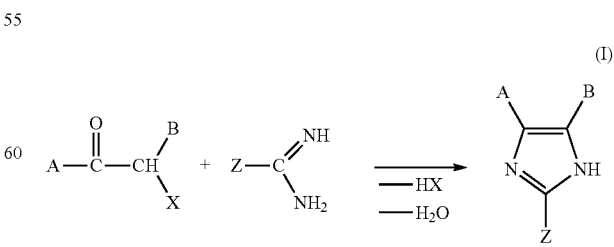
(I)

In the formula, A, B and Z are the same as defined above, and X represents a chlorine atom, a bromine atom or an iodine atom.

The imidazole compounds include:
(A) imidazole compounds in which B is a hydrogen atom and Z is a 2-thienyl group in the chemical formula (I), such as,
4-phenyl-2-(2-thienyl)imidazole,
4-(2-chlorophenyl)-2-(2-thienyl)imidazole,
4-(3-chlorophenyl)-2-(2-thienyl)imidazole,
4-(4-chlorophenyl)-2-(2-thienyl)imidazole,
4-(2,3-dichlorophenyl)-2-(2-thienyl)imidazole,
4-(2,4-dichlorophenyl)-2-(2-thienyl)imidazole,
4-(2,5-dichlorophenyl)-2-(2-thienyl)imidazole,
4-(2,6-dichlorophenyl)-2-(2-thienyl)imidazole,
4-(3,4-dichlorophenyl)-2-(2-thienyl)imidazole,
4-(3,5-dichlorophenyl)-2-(2-thienyl)imidazole,
4-(1-naphthyl)-2-(2-thienyl)imidazole, and
4-(2-naphthyl)-2-(2-thienyl)imidazole;
(B) imidazole compounds in which B is a methyl group and Z is a 2-thienyl group in the chemical formula (I), such as,
5-methyl-4-phenyl-2-(2-thienyl)imidazole,
4-(2-chlorophenyl)-5-methyl-2-(2-thienyl)imidazole,
4-(3-chlorophenyl)-5-methyl-2-(2-thienyl)imidazole,
4-(4-chlorophenyl)-5-methyl-2-(2-thienyl)imidazole,
4-(2,3-dichlorophenyl)-5-methyl-2-(2-thienyl)imidazole,
4-(2,4-dichlorophenyl)-5-methyl-2-(2-thienyl)imidazole,
4-(2,5-dichlorophenyl)-5-methyl-2-(2-thienyl)imidazole,
4-(2,6-dichlorophenyl)-5-methyl-2-(2-thienyl)imidazole,
4-(3,4-dichlorophenyl)-5-methyl-2-(2-thienyl)imidazole,
4-(3,5-dichlorophenyl)-5-methyl-2-(2-thienyl)imidazole,
5-methyl-4-(1-naphthyl)-2-(2-thienyl)imidazole, and
5-methyl-4-(2-naphthyl)-2-(2-thienyl)imidazole;
(C) imidazole compounds in which B is a phenyl group and Z is a 2-thienyl group in the chemical formula (I), such as,
4,5-diphenyl-2-(2-thienyl)imidazole,
4-(2-chlorophenyl)-5-phenyl-2-(2-thienyl)imidazole,
4-(3-chlorophenyl)-5-phenyl-2-(2-thienyl)imidazole,
4-(4-chlorophenyl)-5-phenyl-2-(2-thienyl)imidazole,
4-(2,3-dichlorophenyl)-5-phenyl-2-(2-thienyl)imidazole,
4-(2,4-dichlorophenyl)-5-phenyl-2-(2-thienyl)imidazole,
4-(2,5-dichlorophenyl)-5-phenyl-2-(2-thienyl)imidazole,
4-(2,6-dichlorophenyl)-5-phenyl-2-(2-thienyl)imidazole,
4-(3,4-dichlorophenyl)-5-phenyl-2-(2-thienyl)imidazole,
4-(3,5-dichlorophenyl)-5-phenyl-2-(2-thienyl)imidazole,
4-(1-naphthyl)-5-phenyl-2-(2-thienyl)imidazole, and
4-(2-naphthyl)-5-phenyl-2-(2-thienyl)imidazole;
(D) imidazole compounds in which B is a hydrogen atom and Z is a 3-thienyl group in the chemical formula (I), such as,
4-phenyl-2-(3-thienyl)imidazole,
4-(2-chlorophenyl)-2-(3-thienyl)imidazole,
4-(3-chlorophenyl)-2-(3-thienyl)imidazole,
4-(4-chlorophenyl)-2-(3-thienyl)imidazole,
4-(2,3-dichlorophenyl)-2-(3-thienyl)imidazole,
4-(2,4-dichlorophenyl)-2-(3-thienyl)imidazole,
4-(2,5-dichlorophenyl)-2-(3-thienyl)imidazole,
4-(2,6-dichlorophenyl)-2-(3-thienyl)imidazole,
4-(3,4-dichlorophenyl)-2-(3-thienyl)imidazole,
4-(3,5-dichlorophenyl)-2-(3-thienyl)imidazole,
4-(1-naphthyl)-2-(3-thienyl)imidazole, and
4-(2-naphthyl)-2-(3-thienyl)imidazole;
(E) imidazole compounds in which B is a methyl group and Z is a 3-thienyl group in the chemical formula (I), such as,
5-methyl-4-phenyl-2-(3-thienyl)imidazole,
4-(2-chlorophenyl)-5-methyl-2-(3-thienyl)imidazole,
4-(3-chlorophenyl)-5-methyl-2-(3-thienyl)imidazole,
4-(4-chlorophenyl)-5-methyl-2-(3-thienyl)imidazole,
4-(2,3-dichlorophenyl)-5-methyl-2-(3-thienyl)imidazole,
4-(2,4-dichlorophenyl)-5-methyl-2-(3-thienyl)imidazole,
4-(2,5-dichlorophenyl)-5-methyl-2-(3-thienyl)imidazole,
4-(2,6-dichlorophenyl)-5-methyl-2-(3-thienyl)imidazole,
4-(3,4-dichlorophenyl)-5-methyl-2-(3-thienyl)imidazole,
4-(3,5-dichlorophenyl)-5-methyl-2-(3-thienyl)imidazole,
5-methyl-4-(1-naphthyl)-2-(3-thienyl)imidazole, and
5-methyl-4-(2-naphthyl)-2-(3-thienyl)imidazole;
(F) imidazole compounds in which B is a phenyl group and Z is a 3-thienyl group in the chemical formula (I), such as,
4,5-diphenyl-2-(3-thienyl)imidazole,
4-(2-chlorophenyl)-5-phenyl-2-(3-thienyl)imidazole,
4-(3-chlorophenyl)-5-phenyl-2-(3-thienyl)imidazole,
4-(4-chlorophenyl)-5-phenyl-2-(3-thienyl)imidazole,
4-(2,3-dichlorophenyl)-5-phenyl-2-(3-thienyl)imidazole,
4-(2,4-dichlorophenyl)-5-phenyl-2-(3-thienyl)imidazole,
4-(2,5-dichlorophenyl)-5-phenyl-2-(3-thienyl)imidazole,
4-(2,6-dichlorophenyl)-5-phenyl-2-(3-thienyl)imidazole,
4-(3,4-dichlorophenyl)-5-phenyl-2-(3-thienyl)imidazole,
4-(3,5-dichlorophenyl)-5-phenyl-2-(3-thienyl)imidazole,
4-(1-naphthyl)-5-phenyl-2-(3-thienyl)imidazole, and
4-(2-naphthyl)-5-phenyl-2-(3-thienyl)imidazole;
(G) imidazole compounds in which B is a hydrogen atom and Z is a 2-thienylmethyl group in the chemical formula (I), such as,
4-phenyl-2-(2-thienylmethyl)imidazole,
4-(2-chlorophenyl)-2-(2-thienylmethyl)imidazole,
4-(3-chlorophenyl)-2-(2-thienylmethyl)imidazole,
4-(4-chlorophenyl)-2-(2-thienylmethyl)imidazole,
4-(2,3-dichlorophenyl)-2-(2-thienylmethyl)imidazole,
4-(2,4-dichlorophenyl)-2-(2-thienylmethyl)imidazole,
4-(2,5-dichlorophenyl)-2-(2-thienylmethyl)imidazole,
4-(2,6-dichlorophenyl)-2-(2-thienylmethyl)imidazole,
4-(3,4-dichlorophenyl)-2-(2-thienylmethyl)imidazole,
4-(3,5-dichlorophenyl)-2-(2-thienylmethyl)imidazole,
4-(1-naphthyl)-2-(2-thienylmethyl)imidazole, and
4-(2-naphthyl)-2-(2-thienylmethyl)imidazole;
(H) imidazole compounds in which B is a methyl group and Z is a 2-thienylmethyl group in the chemical formula (I), such as,
5-methyl-4-phenyl-2-(2-thienylmethyl)imidazole,
4-(2-chlorophenyl)-5-methyl-2-(2-thienylmethyl)imidazole,
4-(3-chlorophenyl)-5-methyl-2-(2-thienylmethyl)imidazole,
4-(4-chlorophenyl)-5-methyl-2-(2-thienylmethyl)imidazole,
4-(2,3-dichlorophenyl)-5-methyl-2-(2-thienylmethyl)imidazole,
4-(2,4-dichlorophenyl)-5-methyl-2-(2-thienylmethyl)imidazole,
4-(2,5-dichlorophenyl)-5-methyl-2-(2-thienylmethyl)imidazole,
4-(2,6-dichlorophenyl)-5-methyl-2-(2-thienylmethyl)imidazole,
4-(3,4-dichlorophenyl)-5-methyl-2-(2-thienylmethyl)imidazole,
4-(3,5-dichlorophenyl)-5-methyl-2-(2-thienylmethyl)imidazole,
5-methyl-4-(1-naphthyl)-2-(2-thienylmethyl)imidazole, and
5-methyl-4-(2-naphthyl)-2-(2-thienylmethyl)imidazole;
(I) imidazole compounds in which B is a phenyl group and Z is a 2-thienylmethyl group in the chemical formula (I), such as,
4,5-diphenyl-2-(2-thienylmethyl)imidazole,
4-(2-chlorophenyl)-5-phenyl-2-(2-thienylmethyl)imidazole,
4-(3-chlorophenyl)-5-phenyl-2-(2-thienylmethyl)imidazole,
4-(4-chlorophenyl)-5-phenyl-2-(2-thienylmethyl)imidazole,
4-(2,3-dichlorophenyl)-5-phenyl-2-(2-thienylmethyl)imidazole,
4-(2,4-dichlorophenyl)-5-phenyl-2-(2-thienylmethyl)imidazole, 4-(2,5-dichlorophenyl)-5-phenyl-2-(2-thienylmethyl)imidazole,
4-(2,6-dichlorophenyl)-5-phenyl-2-(2-thienylmethyl)imidazole,
4-(3,4-dichlorophenyl)-5-phenyl-2-(2-thienylmethyl)imidazole,
4-(3,5-dichlorophenyl)-5-phenyl-2-(2-thienylmethyl)imidazole,
4-(1-naphthyl)-5-phenyl-2-(2-thienylmethyl)imidazole, and
4-(2-naphthyl)-5-phenyl-2-(2-thienylmethyl)imidazole;
(J) imidazole compounds in which B is a hydrogen atom and Z is a 3-thienylmethyl group in the chemical formula (I), such as,
4-phenyl-2-(3-thienylmethyl)imidazole,
4-(2-chlorophenyl)-2-(3-thienylmethyl)imidazole,
4-(3-chlorophenyl)-2-(3-thienylmethyl)imidazole,
4-(4-chlorophenyl)-2-(3-thienylmethyl)imidazole,
4-(2,3-dichlorophenyl)-2-(3-thienylmethyl)imidazole,
4-(2,4-dichlorophenyl)-2-(3-thienylmethyl)imidazole,
4-(2,5-dichlorophenyl)-2-(3-thienylmethyl)imidazole,
4-(2,6-dichlorophenyl)-2-(3-thienylmethyl)imidazole,
4-(3,4-dichlorophenyl)-2-(3-thienylmethyl)imidazole,
4-(3,5-dichlorophenyl)-2-(3-thienylmethyl)imidazole,
4-(1-naphthyl)-2-(3-thienylmethyl)imidazole, and
4-(2-naphthyl)-2-(3-thienylmethyl)imidazole;
(K) imidazole compounds in which B is a methyl group and Z is a 3-thienylmethyl group in the chemical formula (I), such as,
5-methyl-4-phenyl-2-(3-thienylmethyl)imidazole,
4-(2-chlorophenyl)-5-methyl-2-(3-thienylmethyl)imidazole,
4-(3-chlorophenyl)-5-methyl-2-(3-thienylmethyl)imidazole,
4-(4-chlorophenyl)-5-methyl-2-(3-thienylmethyl)imidazole,
4-(2,3-dichlorophenyl)-5-methyl-2-(3-thienylmethyl)imidazole,
4-(2,4-dichlorophenyl)-5-methyl-2-(3-thienylmethyl)imidazole,
4-(2,5-dichlorophenyl)-5-methyl-2-(3-thienylmethyl)imidazole,
4-(2,6-dichlorophenyl)-5-methyl-2-(3-thienylmethyl)imidazole,
4-(3,4-dichlorophenyl)-5-methyl-2-(3-thienylmethyl)imidazole,
4-(3,5-dichlorophenyl)-5-methyl-2-(3-thienylmethyl)imidazole,
5-methyl-4-(1-naphthyl)-2-(3-thienylmethyl)imidazole, and
5-methyl-4-(2-naphthyl)-2-(3-thienylmethyl)imidazole;
(L) imidazole compounds in which B is a phenyl group and Z is a 3-thienylmethyl group in the chemical formula (I), such as,
4,5-diphenyl-2-(3-thienylmethyl)imidazole,
4-(2-chlorophenyl)-5-phenyl-2-(3-thienylmethyl)imidazole,
4-(3-chlorophenyl)-5-phenyl-2-(3-thienylmethyl)imidazole,
4-(4-chlorophenyl)-5-phenyl-2-(3-thienylmethyl)imidazole,
4-(2,3-dichlorophenyl)-5-phenyl-2-(3-thienylmethyl)imidazole,
4-(2,4-dichlorophenyl)-5-phenyl-2-(3-thienylmethyl)imidazole,
4-(2,5-dichlorophenyl)-5-phenyl-2-(3-thienylmethyl)imidazole,
4-(2,6-dichlorophenyl)-5-phenyl-2-(3-thienylmethyl)imidazole,
4-(3,4-dichlorophenyl)-5-phenyl-2-(3-thienylmethyl)imidazole,
4-(3,5-dichlorophenyl)-5-phenyl-2-(3-thienylmethyl)imidazole,
4-(1-naphthyl)-5-phenyl-2-(3-thienylmethyl)imidazole, and
4-(2-naphthyl)-5-phenyl-2-(3-thienylmethyl)imidazole.

The surface treating composition of the present invention are prepared by dissolving one or more of the imidazole compounds of formula (I) in water.

In the present invention, a single imidazole compound represented by the above chemical formula (I) can be used alone in the composition, or surface treating compositions can be formed using combinations of two or more of the imidazole compounds. Thus, the surface treating composition of the present invention may comprise one, two, three, four, five, or more, of the imidazole compounds of chemical formula (I). Similarly, the conventional imidazole compounds in the same technical field as the present invention can be also used in combination with one or more of the imidazole compounds of the present invention, i.e., those imidazole compounds of chemical formula (I).

The total amount of imidazole compound present in the surface treating composition is preferably from 0.01 wt % to 10 wt %, and more preferably from 0.1 wt % to 5 wt %. If the amount of imidazole compound contained in the surface treating composition is less than 0.01 wt %, the thickness of the chemical conversion coating formed on the surface of the copper or copper alloy may be decreased, and as a result, oxidation of the surface may not be sufficiently prevented. If the amount of imidazole compound is more than 10 wt %, the imidazole compound may remain undissolved in the surface treating composition, or even where completely dissolved, the imidazole compound may separate out again. If the imidazole compound is not sufficiently dissolved in the surface treating composition, particles of the imidazole compound may attach to the copper or copper alloy surface, and solderability of the surface may be impaired.

In addition to the imidazole compound, the surface treating composition of the present invention may include one or more of the following: (a) a solubilizing agent, (b) an organic solvent, (c) a metal salt, (d) a halogen compound, (e) a metal compound, (f) a coordination compound, (g) an iron compound, and (h) a complex an compound, as auxiliary agents.

As suggested above, a solubilizing agent may be included in the surface treating composition of the present invention. When included, organic acids and/or inorganic acids (hereinafter sometimes merely referred to as "acid") are used as the solubilizing agent.

Representative examples of the organic acid include formic acid, acetic acid, propionic acid, butyric acid, valeric acid, caproic acid, heptanic acid, caprylic acid, pelargonic acid, capric acid, lauric acid, isobutyric acid, 2-ethylbutyric acid, oleic acid, glycolic acid, lactic acid, 2-hydroxybutyric acid, 3-hydroxybutyric acid, gluconic acid, glyceric acid, tartaric acid, malic acid, citric acid, chloroacetic acid, dichloroacetic acid, trichloroacetic acid, bromoacetic acid, iodoacetic acid, methoxyacetic acid, ethoxyacetic acid, propoxyacetic acid, butoxyacetic acid, 2-(2-methoxyethoxy)acetic acid, 2-[2-(2-ethoxyethoxy)ethoxy]acetic acid, 2-{2-[2-(2-ethoxyethoxy)ethoxy]ethoxy}acetic acid, 3-methoxypropionic acid, 3-ethoxypropionic acid, 3-propoxypropionic acid, 3-butoxypropionic acid, levulinic acid, glyoxylic acid, pyruvic acid, acetoacetic acid, acrylic acid, crotonic acid, oxalic acid, malonic acid, succinic acid, glutaric acid, adipic acid, maleic acid, fumaric acid, benzoic acid, p-nitrobenzoic acid, picric acid, salicylic acid, p-toluenesulfonic acid, methanesulfonic acid, and sulfamic acid. Examples of the inorganic acid include hydrochloric acid, phosphoric acid, sulfuric acid, and nitric acid.

The acids can be used alone or in combinations of two or more thereof. Thus, two or more organic acids may be used as a solubilizing agent, two or more inorganic acids may be used as a solubilizing agent, and combinations of one or more organic acids may be used with one or more inorganic acids as a solubilizing agent.

When used, the total amount of solubilizing agent present in the surface treating composition is preferably from 0.1 wt % to 50 wt %, and more preferably from 1 wt % to 30 wt %.

In the present invention, an organic solvent can be used together with the solubilizing agent, or in place of the solubilizing agent.

As the organic solvent, compounds freely miscible with water are preferred. Examples thereof include alcohols such as methanol, ethanol, n-propanol, 2-propanol, n-butanol, or ethylene glycol; cellosolves such as ethylene glycol monomethyl ether, ethylene glycol monoethyl ether or ethylene glycol monobutyl ether; acetone; and N,N-dimethylformamide. These organic solvents can be used alone or in combinations of two or more thereof.

When used, the total amount of organic solvent present in the surface treating composition is preferably from 0.1 wt % to 50 wt %, and more preferably from 1 wt % to 40 wt %.

A metal salt such as a copper compound or a zinc compound can be added as an auxiliary agent to the surface treating composition of the present invention. For example, inclusion of a copper compound as an auxiliary agent in the surface treating composition increases the rate at which the chemical conversion coating is formed on a surface of copper or a copper alloy. Inclusion of a zinc compound as an auxiliary agent in the surface treating composition increases the heat resistance of the chemical conversion coating formed on the surface of copper or a copper alloy.

Examples of copper compounds include copper formate, copper acetate, copper oxalate, copper (I) chloride, copper (II) chloride, copper (I) bromide, copper (II) bromide, copper iodide, copper hydroxide, copper phosphate, copper sulfate, and copper nitrate. A single copper compound, or combinations of two or more copper compounds, can be used as an auxiliary agent.

Examples of zinc compounds include zinc oxide, zinc formate, zinc acetate, zinc oxalate, zinc lactate, zinc citrate, zinc sulfate, zinc nitrate, zinc phosphate, zinc chloride, zinc bromide, and zinc iodide. A single zinc compound, or combinations of two or more zinc compounds, can be used as an auxiliary agent.

When included in the surface treating composition as an auxiliary agent, the copper compound may be present in an amount of preferably from 0.01 wt % to 10 wt %, and more preferably from 0.02 wt % to 5 wt %.

When included in the surface treating composition as an auxiliary agent, the zinc compound may be present in an amount of preferably from 0.01 wt % to 10 wt %, and more preferably from 0.02 wt % to 5 wt %.

In order to further improve the film-forming properties of a chemical conversion coating and the heat resistance of the coating, a halogen compound may be added as an auxiliary agent to the surface treating composition of the present invention.

Examples of halogen compounds include sodium fluoride, potassium fluoride, ammonium fluoride, sodium chloride, potassium chloride, ammonium chloride, chloropropionic acid, sodium bromide, potassium bromide, ammonium bromide, bromopropionic acid, sodium iodide, potassium iodide, ammonium iodide, and iodopropionic acid. A single halogen compound, or a combination of two or more halogen compounds, can be used as an auxiliary agent.

When included in the surface treating composition as an auxiliary agent, the halogen compound may be present in an amount of preferably from 0.001 wt % to 1 wt %, and more preferably from 0.01 wt % to 0.1 wt %.

In addition to the metals salts (i.e., copper compounds and zinc compounds) and halogen compounds described above, a metal compound can be added to the surface treating composition of the present invention as further auxiliary agent. Examples of suitable metal compounds include a manganese compound, a cobalt compound and a nickel compound. Examples of manganese compounds include manganese formate, manganese chloride, manganese oxalate, manganese sulfate and manganese carbonate. Examples of cobalt compounds include cobalt acetate, cobalt sulfate and cobalt nitrate. Examples of nickel compounds include nickel chloride, nickel acetate, nickel nitrate, nickel carbonate, and nickel sulfate. A single metal compound, or a combination of two or more metal compounds, can be used as an auxiliary agent.

When included, the total amount of metal compound present in the surface treating composition is preferably from 0.01 wt % to 10 wt %, and more preferably from 0.02 wt % to 5 wt %.

A coordination compound, such as crown ether, bipyridine, porphyrin or phenanthroline, may also be added as an auxiliary agent to the surface treating composition. The coordination compound functions in denaturating a chemical conversion coating. A single coordination compound, or a combination of two or more coordination compounds, can be used as an auxiliary agent.

When included, the total amount of coordination compound present in the surface treating composition is preferably from 0.001 wt % to 10 wt %, and more preferably from 0.01 wt % to 5 wt %.

An iron compound and a complex an compound (e.g., ethylenediamine tetraacetic acid or the like) can be added as a further auxiliary agent to the surface treating composition of the present invention in order to accelerate formation rate of a chemical conversion coating on a surface of copper while suppressing formation of a chemical conversion coating on a surface of gold (Au) (see JP-A 9-291372, the disclosure of which is incorporated herein by reference).

The pH of the surface treating composition may be set prior to treating a surface of copper or copper alloy. The particular pH of the composition will depend on the constitution (kind and content of components) of the surface treating composition and on the amount of time and the temperature at which the treatment takes place.

In the case of decreasing the pH, the above-described organic acid or inorganic acid (solubilizing agent) can be used, whereas in the case of increasing pH, there can be preferably used, for example, sodium hydroxide, potassium hydroxide, and materials having a buffering action including ammonia and amines such as monoethanolamine, diethanolamine and triethanolamine.

The conditions under which a surface of copper or a copper alloy is treated using the surface treating composition of the present invention are preferably those under which the liquid temperature of the surface treating composition is set to a range of from 10° C. to 70° C. Other conditions include the amount of time with which the copper or copper alloy surface is treated by the surface treating composition. The contact time ranges from 1 second to 10 minutes.

Suitable methods for contacting a surface of copper or a copper alloy with the surface treating composition are not particularly critical to the methods of the present invention and include dipping, spraying and coating. Additional means will be apparent to the skilled artisan.

Examples of the solders that may be used in the methods of the present invention include the conventional Sn—Pb eutectic solders, as well as lead-free solders such as Sn—Ag—Cu based solders, Sn—Ag—Bi based solders, Sn—Bi based solders, Sn—Ag—Bi—In based solders, Sn—Zn based solders, and Sn—Cu based solders.

The soldering method of the present invention can be adaptable to a flow process of running a printed wiring board on a solder bath containing a heat-melted liquid solder to conduct soldering to a joint between an electronic part and the printed wiring board, or a reflow process of previously printing a solder paste to a printed wiring board in conformity with a copper circuit pattern, mounting an electronic part thereon, heating the printed wiring board to melt solder, and conducting soldering.

EXAMPLES

The present invention is specifically described below by reference to Examples and Comparative Examples, but the invention is not construed as being limited thereto.

Imidazole compounds and evaluation test methods employed in Examples and Comparative Examples are as follows.

Imidazole Compound

Imidazole compounds employed in the Examples are as follows.

4-Phenyl-2-(2-thienyl)imidazole (hereinafter abbreviated as "A-1")

5-Methyl-4-phenyl-2-(2-thienyl)imidazole (hereinafter abbreviated as "A-2")

4-(4-Chlorophenyl)-5-methyl-2-(2-thienyl)imidazole (hereinafter abbreviated as "A-3")

4-(2,4-Dichlorophenyl)-5-methyl-2-(2-thienyl)imidazole (hereinafter abbreviated as "A-4")

4-(3,4-Dichlorophenyl)-5-methyl-2-(2-thienyl)imidazole (hereinafter abbreviated as "A-5")

4,5-Diphenyl-2-(2-thienyl)imidazole (hereinafter abbreviated as "A-6")

4-(1-Naphthyl)-2-(2-thienyl)imidazole (hereinafter abbreviated as "A-7")

4-(2-Naphthyl)-2-(2-thienyl)imidazole (hereinafter abbreviated as "A-8")

5-Methyl-4-(1-naphthyl)-2-(2-thienyl)imidazole (hereinafter abbreviated as "A-9")

5-Methyl-4-(2-naphthyl)-2-(2-thienyl)imidazole (hereinafter abbreviated as "A-10")

5-Methyl-4-phenyl-2-(3-thienyl)imidazole (hereinafter abbreviated as "A-11")

5-Methyl-4-phenyl-2-(2-thienylmethyl)imidazole (hereinafter abbreviated as "A-12")

4-(2,4-Dichlorophenyl)-5-methyl-2-(2-thienylmethyl)imidazole (hereinafter abbreviated as "A-13")

4-(3,4-Dichlorophenyl)-5-methyl-2-(2-thienylmethyl)imidazole (hereinafter abbreviated as "A-14")

4-(2-Naphthyl)-2-(2-thienylmethyl)imidazole (hereinafter abbreviated as "A-15")

Methods for producing the exemplified compounds are shown in Reference Examples 2 to 16. Reference Example 1 provides the means for synthesizing 2-thiophenecarboxamidine hydrochloride, which is a raw material used in the production of imidazole compounds beginning with Reference Example 2.

Reference Example 1

Synthesis of 2-thiophenecarboxamidine hydrochloride

To 25 g of dehydrated dichloromethane were added 51.0 g (0.467 mol) of 2-cyanothiophene and 22.6 g (0.49 mol) of dehydrated ethanol and dissolved. To the resulting mixture, 27.4 g (0.752 mol) of hydrogen chloride gas was introduced at 4° C. to 10° C. over 2 hours under ice cooling. Stirring was continued at the same temperature, and as a result, about 2 hours later, crystals were precipitated.

The reaction liquid was allowed to stand in a refrigerator controlled at 5° C. for 3 days, and a solvent was then distilled away under reduced pressure to obtain 89.0 g (0.464 mol, yield: 99.4%) of ethyl 2-thiopheneimidate hydrochloride in wine-colored crystalline bulk state.

The ethyl 2-thiopheneimidate hydrochloride was pulverized, and an ethanol solution obtained by absorbing 13.6 g (0.799 mol) of ammonia into 80 g of dehydrated ethanol was poured thereto little by little under ice cooling, followed by stirring for 4 hours. Then, the temperature was returned to room temperature, and the mixture was further stirred overnight.

A solvent was distilled away from the reaction suspension, a solid concentrate was washed with 300 mL of hexane-dichloromethane (2:1 volume ratio) mixed solution, and dried under reduced pressure, to thereby obtain 72.0 g (0.443 mol, yield 94.8% to 2-cyanothiophene) of 2-thiophenecarboxamidine hydrochloride in slightly wine-colored powder state.

Reference Example 2

Synthesis of A-1

A suspension consisting of 24.4 g (0.15 mol) of 2-thiophenecarboxamidine hydrochloride, 54 g (0.391 mol) of potassium carbonate and 81 g of N,N-dimethylacetamide was stirred at 50° C. for 15 minutes, and a solution consisting of 29.9 g (0.150 mol) of 2-bromoacetophenone and 75 g of toluene was added dropwise thereto at 50° C. to 55° C. over 40 minutes, followed by stirring at 70° C. for 3.5 hours.

The resulting reaction suspension was cooled and then washed with 500 mL of water twice, and solid contents precipitated in the toluene layer were recovered by filtration. The cake recovered was sequentially washed with toluene and water and dried under reduced pressure, to thereby obtain 18.1 g (crude yield 53.3%) of yellowish brown powder.

The powder was recrystallized from acetonitrile to thereby obtain 12.8 g (0.0566 mol, yield 37.7%) of 4-phenyl-2-(2-thienyl)imidazole in cream-colored crystalline state.

Reference Example 3

Synthesis of A-2

A-2 (5-methyl-4-phenyl-2-(2-thienyl)imidazole) was synthesized according to the method of Reference Example 2, except for employing 2-bromopropiophenone in place of 2-bromoacetophenone.

Reference Example 4

Synthesis of A-3

A-3 (4-(4-chlorophenyl)-5-methyl-2-(2-thienyl)imidazole) was synthesized according to the method of Reference Example 2, except for employing 2-bromo-4'-chloropropiophenone in place of 2-bromoacetophenone.

Reference Example 5

Synthesis of A-4

A-4 (4-(2,4-dichlorophenyl)-5-methyl-2-(2-thienyl)imidazole) was synthesized according to the method of Reference Example 2, except for employing 2-bromo-2',4'-dichloropropiophenone in place of 2-bromoacetophenone.

Reference Example 6

Synthesis of A-5

A-5 (4-(3,4-dichlorophenyl)-5-methyl-2-(2-thienyl)imidazole) was synthesized according to the method of Reference Example 2, except for employing 2-bromo-3',4'-dichloropropiophenone in place of 2-bromoacetophenone.

Reference Example 7

Synthesis of A-6

A-6 (4,5-diphenyl-2-(2-thienyl)imidazole) was synthesized according to the method of Reference Example 2, except for employing 2-bromo-2-phenylacetophenone in place of 2-bromoacetophenone.

Reference Example 8

Synthesis of A-7

A-7 (4-(1-naphthyl)-2-(2-thienyl)imidazole) was synthesized according to the method of Reference Example 2, except for employing 2-bromo-1'-acetophenone in place of 2-bromoacetophenone.

Reference Example 9

Synthesis of A-8

A-8 (4-(2-naphthyl)-2-(2-thienyl)imidazole) was synthesized according to the method of Reference Example 2, except for employing 2-bromo-2'-acetophenone in place of 2-bromoacetophenone.

Reference Example 10

Synthesis of A-9

A-9 (5-methyl-4-(1-naphthyl)-2-(2-thienyl)imidazole) was synthesized according to the method of Reference Example 2, except for employing 2-bromo-1'-propionaphthone in place of 2-bromoacetophenone.

Reference Example 11

Synthesis of A-10

A-10 (5-methyl-4-(2-naphthyl)-2-(2-thienyl)imidazole) was synthesized according to the method of Reference Example 2, except for employing 2-bromo-2'-propionaphthone in place of 2-bromoacetophenone.

Reference Example 12

Synthesis of A-11

First, 3-thiophenecarboxamidine hydrochloride was synthesized according to the method of Reference Example 1, except for employing 3-cyanothiophene in place of 2-cyanothiophene.

Then, A-11 (5-methyl-4-phenyl-2-(3-thienyl)imidazole) was synthesized according to the method of Reference Example 2, except for employing 3-thiophenecarboxamidine hydrochloride in place of 2-thiophenecarboxamidine hydrochloride, and 2-bromopropiophenone in place of 2-bromoacetophenone.

Reference Example 13

Synthesis of A-12

First, 2-thienylacetamidine hydrochloride was synthesized according to the method of Reference Example 1, except for employing 2-thiopheneacetonitrile in place of 2-cyanothiophene.

Then, A-12 (5-methyl-4-phenyl-2-(2-thienylmethyl)imidazole) was synthesized according to the method of Reference Example 2, except for employing 2-thienylacetamidine hydrochloride in place of 2-thiophenecarboxamidine hydrochloride, and 2-bromopropiophenone in place of 2-bromoacetophenone.

Reference Example 14

Synthesis of A-13

First, 2-thienylacetamidine hydrochloride was synthesized according to the method of Reference Example 1, except for employing 2-thiopheneacetonitrile in place of 2-cyanothiophene.

Then, A-13 (4-(2,4-dichlorophenyl)-5-methyl-2-(2-thienylmethyl)imidazole) was synthesized according to the method of Reference Example 2, except for employing 2-thienylacetamidine hydrochloride in place of 2-thiophenecarboxamidine hydrochloride, and 2-bromo-2',4"-dichloropropiophenone in place of 2-bromoacetophenone.

Reference Example 15

Synthesis of A-14

First, 2-thienylacetamidine hydrochloride was synthesized according to the method of Reference Example 1, except for employing 2-thiopheneacetonitrile in place of 2-cyanothiophene.

Then, A-14 (4-(3,4-dichlorophenyl)-5-methyl-2-(2-thienylmethyl)imidazole) was synthesized according to the method of Reference Example 2, except for employing 2-thienylacetamidine hydrochloride in place of 2-thiophenecarboxamidine hydrochloride, and 2-bromo-3',4'-dichloropropiophenone in place of 2-bromoacetophenone.

Reference Example 16

Synthesis of A-15

First, 2-thienylacetamidine hydrochloride was synthesized according to the method of Reference Example 1, except for employing 2-thiopheneacetonitrile in place of 2-cyanothiophene.

Then, A-15 (4-(2-naphthyl)-2-(2-thienylmethyl)imidazole) was synthesized according to the method of Reference Example 2, except for employing 2-thienylacetamidine hydrochloride in place of 2-thiophenecarboxamidine hydrochloride, and 2-bromo-2"-acetonaphthone in place of 2-bromoacetophenone.
Chemical formulae of imidazole compounds A-1 to A-15 are shown below.
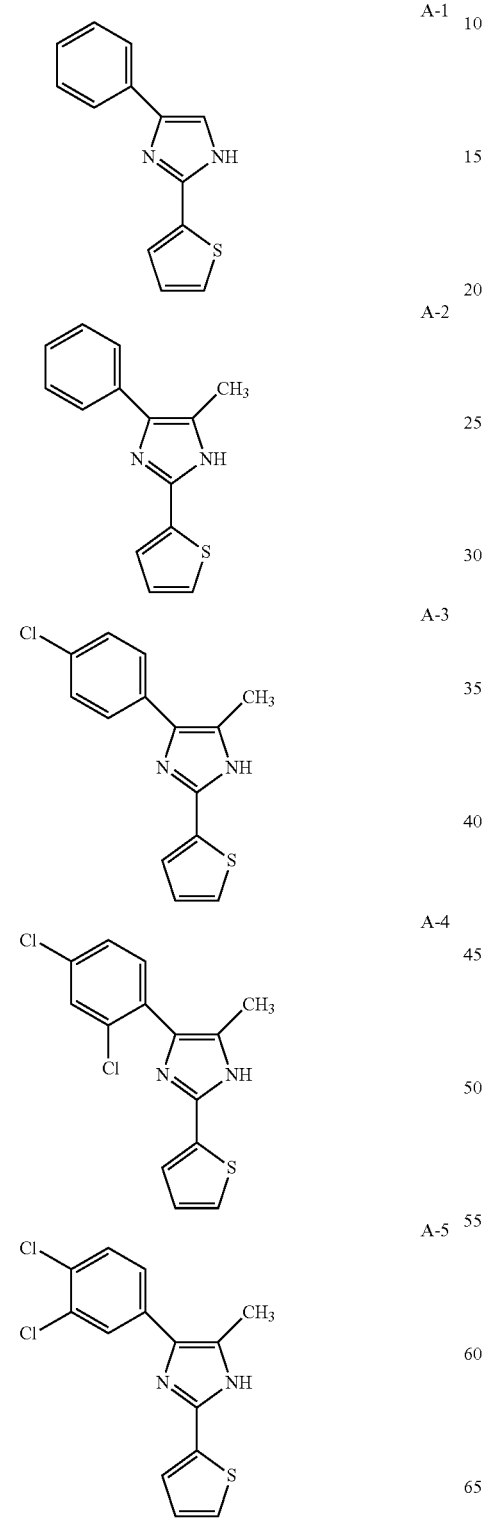
-continued
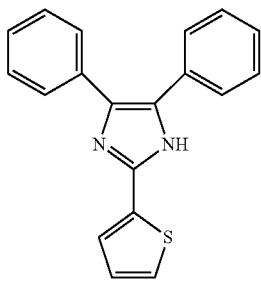
A-6
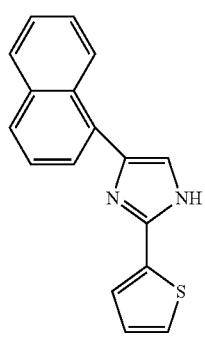
A-7
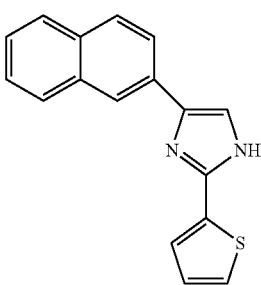
A-8
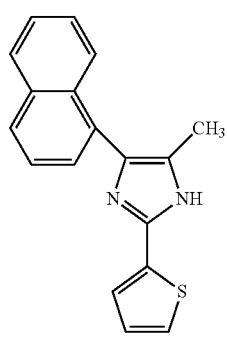
A-9
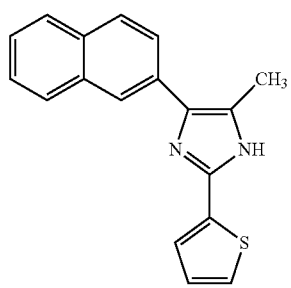
A-10

A-11

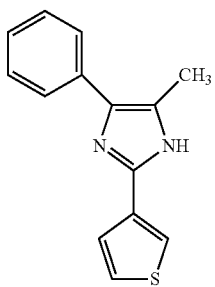

A-12

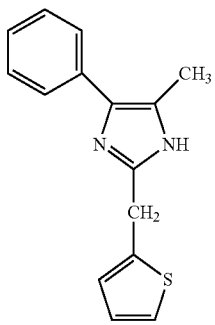

A-13

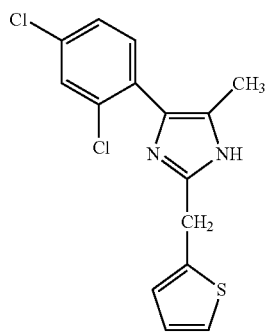

A-14

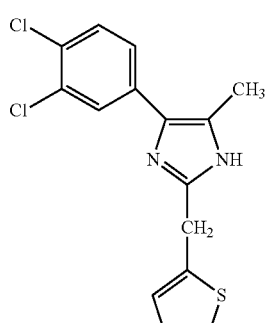

A-15

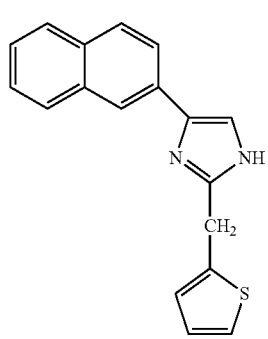

The imidazole compounds employed in the Comparative Examples are as follows.

2-Undecylimidazole (trade name: C11Z, manufactured by Shikoku Chemicals Corporation, hereinafter abbreviated as "Z-1")

2-Benzyl-4-phenylimidazole (synthesized according to the method described in JP-A 2010-150651, hereinafter abbreviated as "Z-2")

2-Phenylimidazole (trade name: 2PZ, manufactured by Shikoku Chemicals Corporation, hereinafter abbreviated as "Z-3")

2-Phenyl-4-methylimidazole (trade name: 2P4MZ, manufactured by Shikoku Chemicals Corporation, hereinafter abbreviated as "Z-4")

2-Nonylbenzimidazole (manufactured by SIGMA-ALDRICH, hereinafter abbreviated as "Z-5")

2-Benzylbenzimidazole (synthesized according to the method described in Science of Synthesis, 12, 529 (2002), hereinafter abbreviated as "Z-6")

The chemical formulae of the imidazole compounds Z-1 to Z-6 are shown below.

Z-1

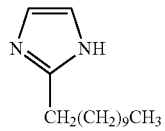

Z-2

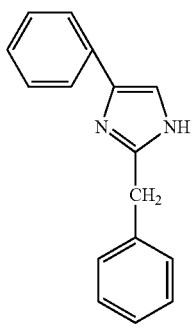

Z-3

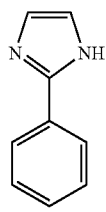

Z-4

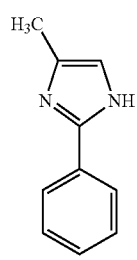

Z-5

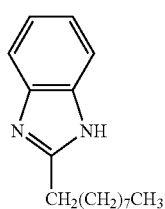

-continued

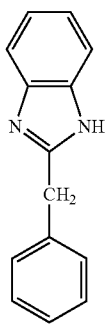

Z-6

Evaluation test methods employed in Examples and Comparative Examples are as follows.

Evaluation Test of Solder Flow-Up Properties

Glass-epoxy resin-made printed wiring board having a size of 120 mm (length)×150 mm (width)×1.6 mm (thickness) and having 300 copper through-holes each having an inner diameter of 0.80 mm was used as a test piece. The test piece was subjected to degreasing, microetching and water washing. Thereafter, the test piece was dipped in a surface treating composition maintained at a given liquid temperature for a given period of time, and then subjected to water washing and drying, to thereby form a chemical conversion coating having a thickness of from about 0.10 μm to 0.50 μm on a surface of copper.

The test piece having been subjected to the surface treatment was subjected to reflow heating, in which the peak temperature was 240° C., three times using an infrared reflow apparatus (product name: MULTI-PRO-306, manufactured by Vitronics), and soldering was then conducted using a flow soldering apparatus (conveyer speed: 1.0 m/min).

The solder employed is Sn—Pb eutectic solder (trade name: H63A, manufactured by Senju Metal Industry Co., Ltd.) having a composition of 63Sn-37Pb (wt %), and flux employed in soldering is JS-64MSS (manufactured by Koki Company Limited). The soldering temperature was 240° C.

Soldering was also conducted to a test piece having been subjected to the surface treatment, employing lead-free solder in the same manner as in the case of the Sn—Pb eutectic solder. The lead-free solder (trade name: H705 ECO SOLDER, manufactured by Senju Metal Industry Co., Ltd.) had a composition of 96.5Sn-3.0Ag-0.5Cu (wt %), and the flux employed in the soldering was JS-E-09 (manufactured by Koki Company Limited). Peak temperature of reflow heating was 245° C., and the soldering temperature was 245° C.

Regarding the test piece having been subjected to soldering, the number of through-holes (soldered through-holes) in which the solder fills the hole to an upper land part of a copper through-hole was counted, and the proportion (%) to the total number of through-holes (300 holes) was calculated.

Molten solder easily permeates copper through-holes and fills the holes to the upper land part of the through-hole with increasing wettability of solder to a surface of copper. That is, it is judged that wettability of solder to copper is more excellent and solderability is better, with an increase in the proportion of the number of through-holes in which solder filled the hole to the upper land part to the total number of through-holes.

Evaluation Test of Solder Spreadability

A glass epoxy resin-made print wiring board having a size of 50 mm (length)×50 mm (width)×1.2 mm (thickness) was used as a test piece. On the test piece, 10 circuit parts each comprising a copper foil and having a conductor width of 0.80 mm and a length of 20 mm had been formed in a width direction at an interval of 1.0 mm as a circuit pattern, in advance. The test piece was subjected to degreasing, microetching and water washing. Thereafter, the test piece was dipped in a surface treating composition maintained at a given liquid temperature for a given period of time, and then subjected to water washing and drying, to thereby form a chemical conversion coating having a thickness of from about 0.10 μm to 0.50 μm on a surface of copper.

The test piece having been subjected to the surface treatment was subjected to reflow heating, in which the peak temperature was 240° C., one time using an infrared reflow apparatus (product name: MULTI-PRO-306, manufactured by Vitronics). Thereafter, Sn—Pb solder paste was printed on the center of the copper circuit part using a metal mask of 1.2 mm aperture diameter and 150 μm thickness, and reflow heating was conducted under the conditions described above, thereby conducting soldering. The Sn—Pb solder paste employed was eutectic solder (trade name: OZ-63-330F-40-10, manufactured by Senju Metal Industry Co., Ltd.) having a composition of 63Sn-37Pb (wt %).

Soldering was also conducted to a test piece having been subjected to the surface treatment, employing lead-free solder paste in the same manner as in the case of the Sn—Pb solder paste. The lead-free solder paste (trade name: M705-221BM5-42-11, manufactured by Senju Metal Industry Co., Ltd.) had a composition of 96.5Sn-3.0Ag-0.5Cu (wt %). The reflow heating conducted before and after the printing of the solder paste was set such that the peak temperature was 245° C.

Regarding the test piece obtained, a length (mm) of solder wet-spread on the copper circuit part was measured.

It is judged that wettability of solder is more excellent and solderability is better, with an increase in the length.

Example 1

Into ion-exchanged water, 4-phenyl-2-(2-thienyl)imidazole as an imidazole compound, acetic acid as an acid (and solubilizing agent), copper acetate and zinc acetate as metal salts, and ammonium chloride and ammonium iodide as halogen compounds were dissolved so as to achieve the constitution (wt %) shown in Table 1, and the resulting solution was adjusted to pH 3.9 with ammonia water to prepare a surface treating composition.

A test piece of a printed wiring board was dipped in the surface treating composition controlled to 40° C. for 90 seconds, washed with water, and dried. Then, solder flow-up properties and solder spreadability were measured. Those test results are shown in Table 1.

Examples 2 to 15

Surface treating compositions having constitutions (wt %) shown in Tables 1 and 2 were prepared using imidazole compounds, acids, metal salts and halogen compounds shown in Tables 1 and 2 in the same manner as in Example 1, and surface treatment was conducted under the treatment conditions shown in Tables 1 and 2. Solder flow-up properties and solder spreadability of the test pieces obtained were measured. Those test results are shown in Tables 1 and 2.

Comparative Examples 1 to 6

Surface treating compositions having the constitutions (wt %) shown in Table 2 were prepared using imidazole compounds, acids, metal salts and halogen compounds shown in Table 2 in the same manner as in Example 1, and surface treatment was conducted under the treatment conditions shown in Table 2. Solder flow-up properties and solder spreadability of the test pieces obtained were measured. Those test results are shown in Table 2.

TABLE 1

| | | | Example | | | | | | | | | |
|---|---|---|---|---|---|---|---|---|---|---|---|---|
| | | | 1 | 2 | 3 | 4 | 5 | 6 | 7 | 8 | 9 | 10 |
| Constitution of surface treating composition (wt %) | Imidazole | (A-1) | 0.25 | — | — | — | — | — | — | — | — | — |
| | | (A-2) | — | 0.25 | — | — | — | — | — | — | — | — |
| | | (A-3) | — | — | 0.25 | — | — | — | — | — | — | — |
| | | (A-4) | — | — | — | 0.25 | — | — | — | — | — | — |
| | | (A-5) | — | — | — | — | 0.25 | — | — | — | — | — |
| | | (A-6) | — | — | — | — | — | 0.25 | — | — | — | — |
| | | (A-7) | — | — | — | — | — | — | 0.25 | — | — | — |
| | | (A-8) | — | — | — | — | — | — | — | 0.25 | — | — |
| | | (A-9) | — | — | — | — | — | — | — | — | 0.25 | — |
| | | (A-10) | — | — | — | — | — | — | — | — | — | 0.25 |
| | Acid | Formic acid | — | — | — | — | — | — | 5 | — | — | — |
| | | Acetic acid | 10 | 10 | 15 | 25 | 25 | 35 | — | 30 | 25 | 10 |
| | | Lactic acid | — | — | — | — | — | — | — | — | — | — |
| | | Levulinic acid | — | — | — | — | — | — | — | — | — | 10 |
| | Metal salt | Copper acetate | 0.10 | 0.10 | 0.10 | — | — | 0.15 | 0.05 | — | — | — |
| | | Copper (II) chloride | — | — | — | 0.08 | 0.08 | — | — | — | — | — |
| | | Copper (II) bromide | — | — | — | — | — | — | — | — | — | — |
| | | Zinc acetate | 1.0 | 3.0 | 2.0 | — | — | — | 2.0 | — | 1.0 | 3.0 |
| | | Zinc chloride | — | — | — | 0.3 | 0.3 | — | — | 0.60 | — | — |
| | Halogen | Ammonium chloride | 0.09 | — | — | — | — | — | — | 0.10 | — | — |
| | | Potassium chloride | — | — | — | — | — | — | 0.15 | — | 0.12 | — |
| | | Ammonium bromide | — | — | — | 0.08 | — | 0.04 | — | — | — | 0.08 |
| | | Potassium bromide | — | — | 0.05 | — | 0.10 | — | — | — | — | — |
| | | Ammonium iodide | 0.02 | — | — | — | — | 0.10 | — | — | — | — |
| | | Potassium iodide | — | 0.08 | 0.06 | — | — | — | 0.02 | — | — | — |
| | | Copper iodide | — | — | — | — | — | — | — | — | — | 0.03 |
| | pH | | 3.9 | 4.0 | 3.6 | 3.2 | 3.3 | 3.0 | 3.3 | 3.3 | 3.3 | 3.4 |
| Treatment condition | Treatment temperature (° C.) | | 40 | 40 | 40 | 40 | 30 | 40 | 40 | 35 | 40 | 40 |
| | Treatment time (second) | | 90 | 60 | 120 | 120 | 180 | 180 | 90 | 180 | 180 | 60 |
| Evaluation Test | Solder flow-up properties (%) | Eutectic solder | 98 | 97 | 98 | 88 | 92 | 87 | 100 | 92 | 88 | 100 |
| | | Lead-free solder | 94 | 90 | 91 | 84 | 85 | 83 | 98 | 85 | 82 | 96 |
| | Solder spreadability (mm) | Eutectic solder | 3.31 | 3.17 | 3.12 | 3.15 | 3.55 | 3.24 | 3.57 | 3.41 | 3.08 | 3.61 |
| | | Lead-free solder | 1.68 | 1.66 | 1.64 | 1.58 | 1.70 | 1.62 | 1.71 | 1.69 | 1.59 | 1.70 |

TABLE 2

| | | | Example | | | | | Comparative Example | | | | | |
|---|---|---|---|---|---|---|---|---|---|---|---|---|---|
| | | | 11 | 12 | 13 | 14 | 15 | 1 | 2 | 3 | 4 | 5 | 6 |
| Constitution of surface treating composition (wt %) | Imidazole | (A-11) | 0.25 | — | — | — | — | — | — | — | — | — | — |
| | | (A-12) | — | 0.25 | — | — | — | — | — | — | — | — | — |
| | | (A-13) | — | — | 0.25 | — | — | — | — | — | — | — | — |
| | | (A-14) | — | — | — | 0.20 | — | — | — | — | — | — | — |
| | | (A-15) | — | — | — | — | 0.25 | — | — | — | — | — | — |
| | | (Z-1) | — | — | — | — | — | 1.0 | — | — | — | — | — |
| | | (Z-2) | — | — | — | — | — | — | 0.30 | — | — | — | — |
| | | (Z-3) | — | — | — | — | — | — | — | 1.0 | — | — | — |
| | | (Z-4) | — | — | — | — | — | — | — | — | 1.0 | — | — |
| | | (Z-5) | — | — | — | — | — | — | — | — | — | 0.2 | — |
| | | (Z-6) | — | — | — | — | — | — | — | — | — | — | 3.0 |
| | Acid | Formic acid | — | 4 | 16 | 2 | 5 | — | — | — | — | — | 3 |
| | | Acetic acid | 10 | — | — | 10 | 10 | 2 | 10 | 2 | 2 | 5 | — |
| | | Lactic acid | — | — | 2 | — | — | — | — | — | — | — | — |
| | | Levulinic acid | — | — | — | — | — | — | — | — | — | — | — |
| | Metal salt | Copper acetate | 0.10 | 0.20 | 0.20 | — | — | 0.10 | 0.20 | — | — | — | — |
| | | Copper (II) chloride | — | — | — | — | — | — | — | — | 0.08 | — | — |
| | | Copper (II) bromide | — | — | — | — | 0.80 | — | — | 0.10 | — | — | 0.05 |
| | | Zinc acetate | — | — | — | 1.0 | — | 1.00 | — | — | — | — | — |
| | | Zinc chloride | — | — | 0.60 | — | — | — | — | — | — | 0.20 | — |

TABLE 2-continued

| | | | Example | | | | | Comparative Example | | | | | |
|---|---|---|---|---|---|---|---|---|---|---|---|---|---|
| | | | 11 | 12 | 13 | 14 | 15 | 1 | 2 | 3 | 4 | 5 | 6 |
| | Halogen | Ammonium chloride | 0.10 | — | 0.10 | — | — | — | 0.10 | — | — | — | — |
| | | Potassium chloride | — | — | — | — | — | — | — | — | — | — | — |
| | | Ammonium bromide | — | — | — | — | — | 0.07 | — | — | — | — | — |
| | | Potassium bromide | — | 0.05 | — | — | — | — | — | — | — | — | — |
| | | Ammonium iodide | — | — | — | 0.01 | — | — | — | — | — | — | — |
| | | Potassium iodide | 0.08 | 0.10 | — | — | — | — | — | — | — | 0.02 | — |
| | | Copper iodide | — | — | 0.02 | — | — | — | — | — | — | — | — |
| | pH | | 4.0 | 3.7 | 2.8 | 2.8 | 2.3 | 4.4 | 4.0 | 4.8 | 4.6 | 2.9 | 2.9 |
| Treatment condition | Treatment temperature (° C.) | | 40 | 40 | 40 | 40 | 30 | 30 | 40 | 50 | 50 | 40 | 40 |
| | Treatment time (second) | | 90 | 90 | 180 | 60 | 300 | 20 | 120 | 180 | 60 | 180 | 120 |
| Evaluation Test | Solder flow-up properties | Eutectic solder | 97 | 87 | 95 | 98 | 87 | 28 | 52 | 55 | 61 | 72 | 64 |
| | | Lead-free solder | 93 | 82 | 91 | 95 | 81 | 11 | 27 | 21 | 27 | 40 | 32 |
| | Solder spreadability (mm) | Eutectic solder | 3.32 | 3.11 | 3.26 | 3.42 | 3.07 | 2.14 | 2.34 | 2.24 | 2.31 | 2.35 | 2.28 |
| | | Lead-free solder | 1.68 | 1.56 | 1.64 | 1.66 | 1.58 | 1.37 | 1.41 | 1.42 | 1.41 | 1.44 | 1.47 |

The surface treating composition of the present invention can be used in soldering using Sn—Pb eutectic solder without any problems, and can further preferably be used in soldering using lead-free solder having poor solderability as compared with that of the eutectic solder.

While the present invention has been described in detail and with reference to specific embodiments thereof, it will be apparent to one skilled in the art that various changes and modifications can be made therein without departing from the spirit and scope thereof.

The present application is based on Japanese patent application No. 2011-114289 filed on May 23, 2011, the entire contents of which are incorporated hereto by reference. All references cited herein are incorporated in their entirety.

INDUSTRIAL APPLICABILITY

According to the present invention, a surface treating composition which allows good solderability by forming a chemical conversion coating having good heat resistance and wettability to solder on a surface of copper or a copper alloy constituting a circuit part and the like of a printed wiring board is disclosed. The surface treating composition permits joining of electronic parts and the like to a printed wiring board using a solder. A surface treating method, a printed wiring board and a soldering method are also provided.

What is claimed is:

1. A printed wiring board comprising at least one circuit part,
   wherein the circuit part comprises copper or a copper alloy and a chemical conversion coating on a surface of the copper or the copper alloy, and
   wherein the coating is formed by contacting the surface of the copper or the copper alloy with a surface treating composition comprising an imidazole compound represented by the chemical formula (I):

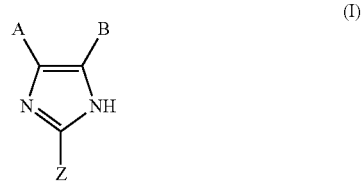

wherein A represents a group represented by formula (II) or a group represented by formula (III), B represents a hydrogen atom, a methyl group or a phenyl group, and Z represents a group represented by formula (IV) or a group represented by formula (V),

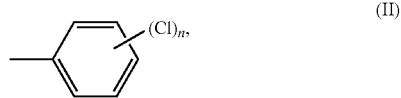

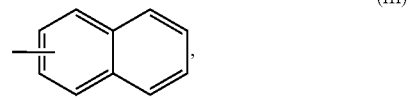

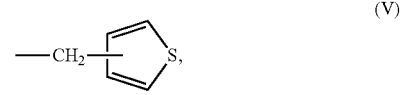

wherein n is 0, 1 or 2.

2. The printed wiring board according to claim 1,
   wherein the imidazole compound is present in the composition in an amount of from 0.01 wt % to 10 wt %.

3. The printed wiring board according to claim 1,
   wherein the surface treating composition further comprises an organic acid or an inorganic acid, present in the composition in an amount of from 0.1 wt % to 50 wt %.

4. The printed wiring board according to claim 1,
wherein the surface treating composition further comprises a metal salt, present in the composition in an amount of from 0.01 wt % to 10 wt %.

5. The printed wiring board according to claim 1,
wherein the surface treating composition further comprises a halogen compound, present in the composition in an amount of from 0.001 wt % to 1 wt %.

6. The printed wiring board according to claim 3,
wherein the organic acid is at least one selected from the group consisting of formic acid, acetic acid, propionic acid, butyric acid, valeric acid, caproic acid, heptanic acid, caprylic acid, pelargonic acid, capric acid, lauric acid, isobutyric acid, 2-ethylbutyric acid, glycolic acid, lactic acid, 2-hydroxybutyric acid, 3-hydroxybutyric acid, gluconic acid, glyceric acid, tartaric acid, malic acid, citric acid, chloroacetic acid, dichloroacetic acid, trichloroacetic acid, bromoacetic acid, iodoacetic acid, methoxyacetic acid, ethoxyacetic acid, propoxyacetic acid, butoxyacetic acid, 2-(2-methoxyethoxy)acetic acid, 2-[2-(2-ethoxyethoxy)ethoxy]acetic acid, 2-{2-[2-(2-ethoxyethoxy)ethoxy]ethoxy}acetic acid, 3-methoxypropionic acid, 3-ethoxypropionic acid, 3-propoxypropionic acid, 3-butoxypropionic acid, levulinic acid, glyoxylic acid, pyruvic acid, acetoacetic acid, acrylic acid, crotonic acid, oxalic acid, malonic acid, succinic acid, glutaric acid, adipic acid, maleic acid, fumaric acid, benzoic acid, p-nitrobenzoic acid, picric acid, salicylic acid, p-toluenesulfonic acid, methanesulfonic acid, and sulfamic acid; and
wherein the inorganic acid is at least one selected from the group consisting of hydrochloric acid, phosphoric acid, sulfuric acid, and nitric acid.

* * * * *